(12) United States Patent
Pelzer et al.

(10) Patent No.: US 6,804,547 B2
(45) Date of Patent: Oct. 12, 2004

(54) MEDICAL THERAPEUTIC AND/OR DIAGNOSTIC APPARATUS HAVING A POSITION DETECTING DEVICE

(75) Inventors: Martin Pelzer, Zang (DE); Walter Neubrandt, Zang (DE); Joachim Luber, Essingen (DE); Arvids Mackevics, Aalen (DE)

(73) Assignee: Carl-Zeiss-Stiftung, Heidenheim (DE)

( * ) Notice: Subject to any disclaimer, the term of this patent is extended or adjusted under 35 U.S.C. 154(b) by 241 days.

(21) Appl. No.: 09/960,997

(22) Filed: Sep. 25, 2001

(65) Prior Publication Data

US 2002/0038084 A1 Mar. 28, 2002

(30) Foreign Application Priority Data

Sep. 25, 2000 (DE) .......................................... 100 47 698

(51) Int. Cl.[7] .............................. A61B 5/00; A61B 6/00
(52) U.S. Cl. ...................... 600/424; 600/476; 606/130
(58) Field of Search ............................... 600/414, 426, 600/424, 476, 411, 407, 427, 429, 425, 300, 595; 606/130

(56) References Cited

U.S. PATENT DOCUMENTS

| 5,383,454 | A | | 1/1995 | Bucholz |
| 5,408,409 | A | | 4/1995 | Glassman et al. |
| 5,772,594 | A | * | 6/1998 | Barrick ........................ 600/407 |
| 5,790,307 | A | * | 8/1998 | Mick et al. .................. 359/382 |
| 5,891,020 | A | * | 4/1999 | Luber et al. ................. 600/300 |
| 5,921,992 | A | * | 7/1999 | Costales et al. ............ 606/130 |
| 5,938,602 | A | * | 8/1999 | Lloyd ........................... 600/424 |
| 6,161,033 | A | * | 12/2000 | Kuhn ........................... 600/429 |
| 6,183,415 | B1 | * | 2/2001 | Gartner ....................... 600/300 |
| 6,226,546 | B1 | * | 5/2001 | Evans .......................... 600/424 |
| 6,618,612 | B1 | * | 9/2003 | Acker et al. ................. 600/424 |

FOREIGN PATENT DOCUMENTS

| DE | 197 51 781 | 5/1998 |
| DE | 198 37 152 | 4/1999 |

* cited by examiner

*Primary Examiner*—Shawna J. Shaw
(74) *Attorney, Agent, or Firm*—Walter Ottesen

(57) ABSTRACT

The invention is directed to a medical therapeutic and/or diagnostic apparatus having a function unit (1) and a position detecting device (5). A further detecting device (7) is mounted so as to be fixed in position and orientation and is separated from the position detecting device (5) by a signal path. The position detecting device (5) operates together with the additional detecting device (7). The position detecting device (5) can be changed during operation with respect to position and orientation relative to the function unit (1).

11 Claims, 2 Drawing Sheets

MEDICAL THERAPEUTIC AND/OR DIAGNOSTIC APPARATUS HAVING A POSITION DETECTING DEVICE

FIELD OF THE INVENTION

The invention relates to a medical therapeutic and/or diagnostic apparatus having a function unit. The diagnostic apparatus also includes a first detecting device for detecting positions and a second detecting device which coacts with the first detecting device. The second detecting device is separated from the first detecting device by a signal path and is mounted so as to be stationary with respect to both position and orientation.

BACKGROUND OF THE INVENTION

A therapeutic and/or diagnostic apparatus of the kind described above is disclosed, for example, in U.S. Pat. No. 5,408,409. This apparatus has a function unit, which is configured as a surgical cutting tool, on which an LED arrangement is mounted which functions as a position detecting device. A further detecting device is spaced therefrom and is configured as a camera arrangement fixed with respect to position and orientation.

Additional therapeutic and/or diagnostic apparatus having a function unit configured as a surgical microscope are described in German patent publication 197 51 781 and U.S. Pat. No. 6,183,415.

SUMMARY OF THE INVENTION

It is an object of the invention to provide a therapeutic and/or diagnostic apparatus which is improved with respect to the accuracy of the detection of position. It is a further object of the invention to improve the apparatus of the invention so that it is less sensitive to disturbances.

The medical therapeutic and/or diagnostic apparatus of the invention includes: a function unit; a first detecting device associated with the function unit; a second detecting device for coacting with the first detecting device and being mounted so as to be stationary in position and orientation; the second detecting device being separated from the first detecting device by a signal path; and, the first detecting device being mounted so as to be movable relative to the function unit so as to be changeable with respect to both position and orientation.

Because of the change of position and orientation of the position detecting device relative to the function unit during work with the apparatus, the signal path can be optimized to avoid shading while considering the particular operating situation by selecting a suitable position for the position detecting device relative to the function unit. The shading is caused, for example, by medical personnel during a medical procedure.

In one embodiment, the position detecting device is in the form of a position detecting arm having a transmitting unit with active markers, for example, at least three transmitting elements arranged so as to be spatially distributed. These transmitting elements can be LEDs or ultrasonic transmitters. The position detecting device can, however, also include passive markers (for example, reflecting surfaces) which can be detected by an additional detecting device.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
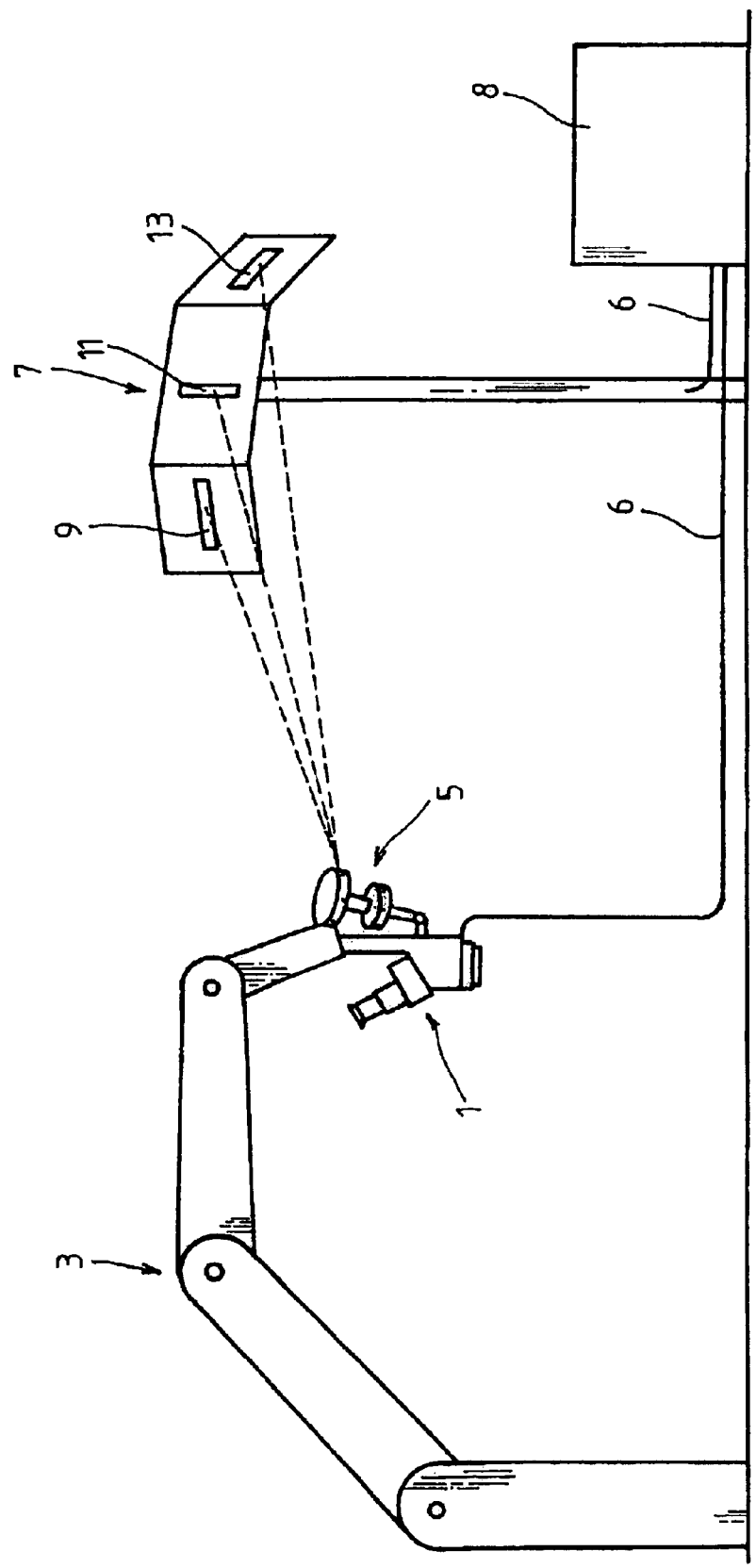
FIG. 1 shows an embodiment of the invention in the form of a surgical microscope; and, FIG. 2 is a perspective view of the surgical microscope of FIG. 1 equipped with a probe.

FIG. 1 shows a medical therapeutic and/or diagnostic apparatus 1 in the form of a surgical microscope which is displaceable and pivotable via an articulated stand 3. A position and orientation detecting arrangement is provided for detecting the particular orientation of the surgical microscope 1 and includes a first detecting device 5 for detecting position mounted on the surgical microscope 1 and a second detecting device 7 which is stationary and fixed in position and orientation. The first detecting device 5 and the second detecting device 7 are connected to a position evaluation unit 8 via lines 6 indicated schematically. The position and orientation detection, which forms the basis of the invention, is based on a direct signal transmission (for example, via light or ultrasonic sound) between the first detecting device 5 and the second detecting device 7. For this reason, the second detecting device 7 is to be mounted in such a manner that the signal path to the first detecting device 5 is free of obstructions. The second detecting device 7 is configured in this embodiment as an arrangement of three line cameras (9, 11, 13) and the first detecting device 5 is configured as a transmitting unit.

Figure 2:
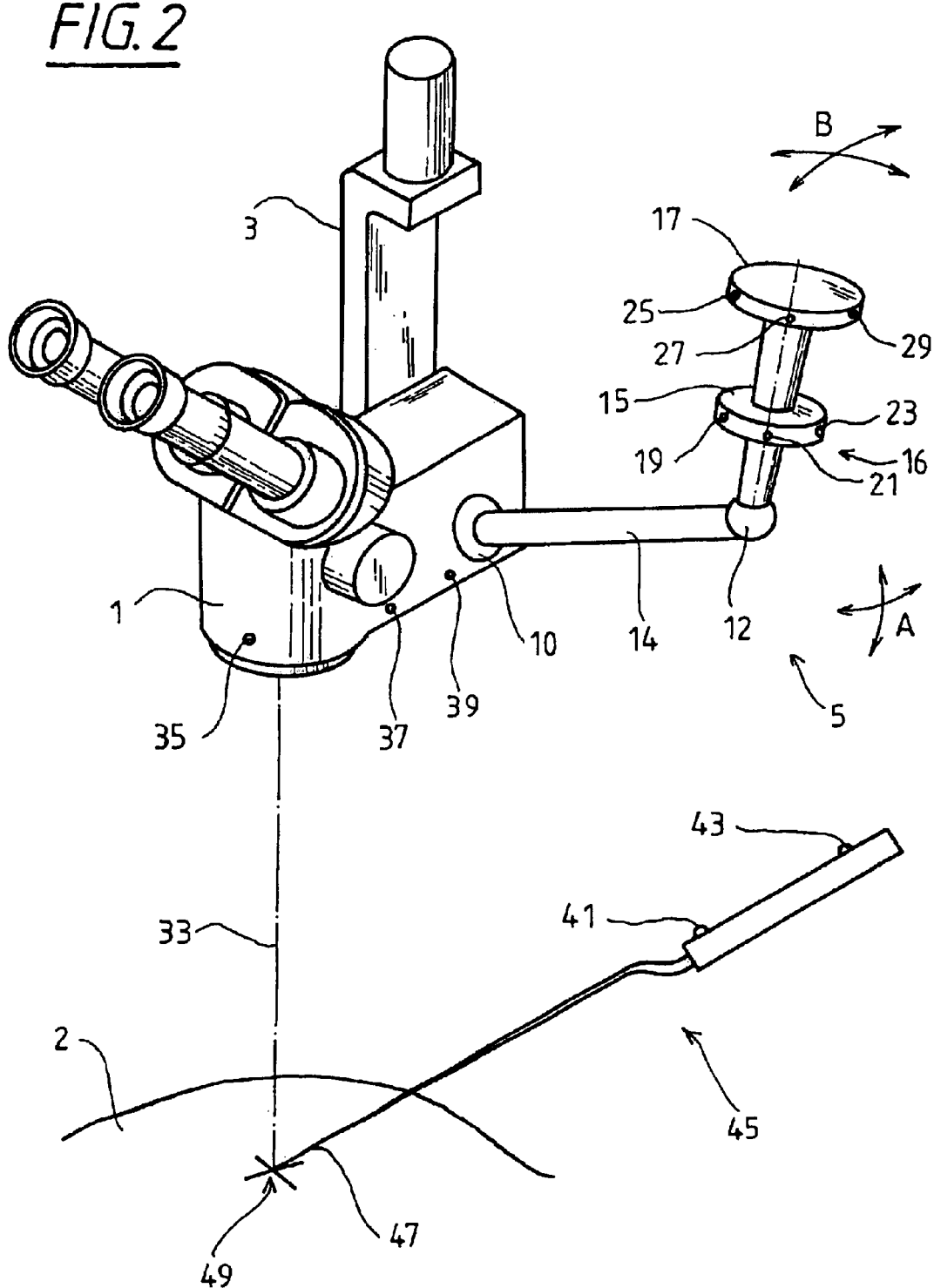

In FIG. 2, the position detecting unit is shown configured as a position detecting assembly 5 in accordance with the invention. The position detecting assembly and the surgical microscope 1 are shown together with a probe 45 and an object 2 under observation.

The position detecting assembly 5 includes an elongated extension arm 14 and a position detecting part 16. The position detecting part 16 includes a first radial projection 15 and a second radial projection 17 mounted at a spacing from the first radial projection.

Transmitting elements are arranged on the peripheral edge of the respective radial projections 15 and 17. In this case, the transmitting elements are LEDs. The transmitting elements 19, 21 and 23 are arranged on radial projection 15 and the transmitting elements 25, 27 and 29 are arranged on radial projection 17.

The extension arm 14 is mounted on the surgical microscope 1 with a ball-and-socket joint 10 and is therefore pivotable in the directions of the double arrow A. The position detecting part 16 is attached to the extension arm 14 with a second ball-and-socket joint 12. The position detecting part 16 is pivotable relative to the extension arm 14 in the direction of double arrow B because of the second ball-and-socket joint 12.

Alternatively, or in addition, the position detecting assembly 5 can also be configured as displaceable relative to the surgical microscope 1.

The position and orientation evaluating unit 8 must always be informed as to the particular relative orientation of the position detecting assembly 5 to the surgical microscope 1. This is achieved, for example, by angular sensors, which are mounted in the joints 10 and 12. The angular sensors have a signal line to the position evaluation unit 8.

The method which follows can also be carried out with a probe 45 disclosed in U.S. Pat. No. 5,383,454 incorporated herein by reference.

The handheld probe 45 includes two transmitting elements 41 and 43 which lie on a straight line together with the probe tip 47 and can be detected with respect to orientation by the second detecting device 7. The spacings of the probe tip 47 to the transmitting elements 41 and 43 are known to the position evaluation unit 8. For this reason, the position of the probe tip can be determined from the orientation of the transmitting elements 41 and 43.

The coordinates of the measuring points 35, 37 and 39 on the surgical microscope 1 with respect to the detecting device 7 are determined in that these points are probed by the probe tip 47 by activating the transmitting elements 41 and 43. Then the orientation and/or position of the position detecting assembly 5 is determined with respect to the detecting device 7 by activating the transmitting elements 19, 21, 23, 25, 27 and 29 of the position detecting assembly 5. From this, the position evaluation unit 8 can then compute the relative orientation of the position detecting assembly 5 to the surgical microscope.

The orientational relationships of the contact points 35, 37 and 39 to the optical axis 33 of the surgical microscope are fixed and known. For this reason, the positional and orientational relationship of the position detecting assembly 5 to the focus 49 of the surgical microscope 1 can be determined from this known orientational relationship of the measuring points 35, 37 and 39 to the optical axis 33 especially together with the data as to the particular focal intercept of the surgical microscope 1.

Supplementarily or alternatively, the focus 49 can be contacted directly with the pointer 45 as shown. The focus 49 can be recognized with the surgical microscope 1, for example, based on the crosslines shown and, in this way, the positional and orientational relationship of the position detecting assembly 5 to the focus 49 of the surgical microscope 1 can be determined with increased accuracy and/or without contacting the measuring points 35, 37 and 39 on the surgical microscope 1.

It is understood that the foregoing description is that of the preferred embodiments of the invention and that various changes and modifications may be made thereto without departing from the spirit and scope of the invention as defined in the appended claims.

What is claimed is:

1. A medical therapeutic and/or diagnostic apparatus comprising:
   a function unit in the form of a therapeutic and/or diagnostic instrument;
   a first detecting device associated with said function unit;
   a second detecting device for coacting with said first detecting device and being mounted so as to be stationary in position and orientation;
   said second detecting device being separated from said first detecting device by an optical signal path or an ultrasonic signal path; and,
   said first detecting device being mounted on said function unit so as to physically movable relative to said function unit so as to be changeable with respect to both position and orientation.

2. The medical therapeutic and/or diagnostic apparatus of claim 1, wherein said maid function unit is a surgical microscope.

3. The medical therapeutic and/or diagnostic apparatus of claim 1, wherein said first detecting device is configured as a position detecting assembly extending from said function unit.

4. The medical therapeutic and/or diagnostic apparatus of claim 3, wherein said position detecting assembly comprises a transmitting unit having at least three transmitting elements arranged so as to be spatially distributed.

5. The medical therapeutic and/or diagnostic apparatus of claim 1, wherein said function unit has measuring points.

6. The medical therapeutic and/or diagnostic apparatus of claim 1, wherein said signal path is a clear uninterrupted line-of-sight path.

7. A medical therapeutic and/or diagnostic apparatus comprising:
   a function unit;
   a first detecting device associated with said function unit;
   a second detecting device for coacting with said first detecting device and being mounted so as to be stationary in position and orientation;
   said second detecting device being separated from said first detecting device by a signal path;
   said first detecting device being mounted so as to be movable relative to said function unit so as to be changeable with respect to both position and orientation; and,
   said position detecting assembly including an extension arm and a ball-and-socket joint for connecting said extension arm to said function unit.

8. The medical therapeutic and/or diagnostic apparatus of claim 7, wherein said ball-and-socket joint is a first ball-and-socket joint; and, said position detecting assembly further comprises a position detecting part and a second ball-and-socket joint for connecting said position detecting part to said extension arm.

9. A medical therapeutic and/or diagnostic apparatus comprising:
   a function unit in the form of an optical surgical instrument;
   a first detecting device associated with said function unit;
   a second detecting device for coacting with said first detecting device and being mounted so as to be stationary in position and orientation;
   said second detecting device being separated from said first detecting device by an optical signal path; and,
   said first detecting device being mounted on said function unit so as to be physically movable relative to said function unit so as to be changeable with respect to both position and orientation relative to said function unit.

10. A medical therapeutic and/or diagnostic apparatus comprising:
    a surgical microscope;
    a first detecting device associated with said surgical microscope;
    a second detecting device for coacting with said first detecting device and being mounted so as to be stationary in position and orientation;
    said second detecting device being separated from said first detecting device by a signal path; and,
    said first detecting device being mounted on said surgical microscope so as to be physically movable relative to said function unit so as to be changeable with respect to both position and orientation.

11. The medical therapeutic and/or diagnostic apparatus of claim 10, wherein the first detecting device is configured as a position detecting assembly extending from said surgical microscope.

* * * * *

UNITED STATES PATENT AND TRADEMARK OFFICE
CERTIFICATE OF CORRECTION

PATENT NO. : 6,804,547 B2
DATED : October 12, 2004
INVENTOR(S) : Martin Pelzer et al.

Page 1 of 1

It is certified that error appears in the above-identified patent and that said Letters Patent is hereby corrected as shown below:

Column 3,
Line 60, delete "maid" and substitute -- said -- therefor.

Signed and Sealed this

Fifteenth Day of February, 2005

JON W. DUDAS
*Director of the United States Patent and Trademark Office*